(12) United States Patent
Reitz et al.

(10) Patent No.: US 6,777,566 B2
(45) Date of Patent: Aug. 17, 2004

(54) PROCESS FOR PRODUCING PLATINUM ALKENYL POLYSILOXANE COMPLEX COMPOUNDS, ESPECIALLY PLATINUM DIVINYLTETRAMETHYLDISILOXANE

(75) Inventors: Ramona Reitz, Biebergemünd (DE); Richard Walter, Alzenau (DE)

(73) Assignee: W. C. Heraeus GmbH & Co. KG (DE)

( * ) Notice: Subject to any disclaimer, the term of this patent is extended or adjusted under 35 U.S.C. 154(b) by 0 days.

(21) Appl. No.: 10/272,569

(22) Filed: Oct. 16, 2002

(65) Prior Publication Data

US 2003/0073859 A1 Apr. 17, 2003

(30) Foreign Application Priority Data

Oct. 16, 2001 (DE) .......................................... 101 50 489

(51) Int. Cl.$^7$ ........................... C07F 19/00; B01J 31/28; C08G 77/00
(52) U.S. Cl. ............................. 556/10; 556/12; 528/10; 528/15; 502/154; 502/158
(58) Field of Search ....................... 556/10, 12; 258/10, 258/15; 502/154, 158; 528/10

(56) References Cited

U.S. PATENT DOCUMENTS

| 3,715,334 A | 2/1973 | Karstedt .............. 260/46.5 AU |
| 6,589,903 B2 * | 7/2003 | Reitz et al. ................. 502/158 |
| 2002/0099159 A1 | 7/2002 | Reitz et al. .................... 528/10 |

FOREIGN PATENT DOCUMENTS

| DE | 100 35 644 C1 * | 12/2001 |
| EP | 0 894 804 A2 * | 2/1999 |
| EP | 979 837 | 2/2000 |
| EP | 0 979 837 A2 * | 2/2000 |

* cited by examiner

Primary Examiner—Porfirio Nazario-Gonzalez
(74) Attorney, Agent, or Firm—Ostrolenk, Faber, Gerb & Soffen, LLP

(57) ABSTRACT

A process for producing platinum alkenyl polysiloxane complex compounds, especially platinum divinyltetramethyldisiloxane, by reacting a haloplatinum compound with at least one alkenyl polysiloxane in the initial presence of platinum in the form of a platinum complex compound as an autocatalyst and in the initial presence of at least one base in an organic solvent or mixture of organic solvents that can be oxidized by the haloplatinum compound.

17 Claims, No Drawings

PROCESS FOR PRODUCING PLATINUM ALKENYL POLYSILOXANE COMPLEX COMPOUNDS, ESPECIALLY PLATINUM DIVINYLTETRAMETHYLDISILOXANE

BACKGROUND OF THE INVENTION

The invention concerns a process for producing platinum alkenyl polysiloxane complex compounds, platinum alkenyl polysiloxane complex compounds produced by this process, especially platinum divinyltetramethyldisiloxane produced by this process, and several uses.

EP 0 979 837 A2 discloses a process for producing a platinum hydrosilylation catalyst, in which a mixture that contains haloplatinic acid, alkenyl polysiloxane, and cycloalkyl polysiloxane is first stirred at a certain temperature, then treated with sufficient alkali to remove essentially the halogen, and then filtered to obtain the corresponding platinum hydrosilylation catalyst, and in which, furthermore, 0.3 to about 20 moles of cycloalkyl polysiloxane must be supplied per mole of alkenyl polysiloxane. In this process, the reaction temperature for the production of the platinum divinylsiloxane hydrosilylation catalyst (Karstedt's catalyst) is 70° C.

SUMMARY AND DESCRIPTION OF THE INVENTION

The object of the present invention is to provide a process in which the reaction temperature can be kept low, and undesired product impurities can be avoided as far as possible.

In accordance with the invention, this goal is achieved by the process in which a haloplatinum compound is first reacted with at least one alkenyl polysiloxane in the initial presence of platinum in the form of a platinum complex compound as an autocatalyst and in the initial presence of at least one base, especially a bicarbonate, carbonate or hydroxide, at the lowest possible temperature in an organic solvent or mixture of organic solvents that can be oxidized by the haloplatinum compound.

As a rule, the reaction mixture is stirred during the reaction, e.g., by a magnetic stirrer, to provide better mixing and to avoid local overheating. The individual reactants are fed into the reaction mixture, for example, in portions or by drops. The product is recovered by standard methods, say, by separating solid particles from the liquid phase and then concentrating the liquid phase. After the reaction, the customary procedure is to filter the reaction mixture and concentrate the filtrate. The liquid phase contains the reaction product, platinum alkenyl polysiloxane.

Central to the invention is the surprising finding that, when small amounts of platinum alkenyl polysiloxane are present at the start of the reaction, the reaction itself is autocatalyzed, so that the usual reaction temperature can be lowered by as much as 20 K or so, with the result that the actual product is contaminated (with respect to color as well) by fewer decomposition products and by-products. Undesired precipitation of platinum is reduced or entirely suppressed. Furthermore, the lower temperatures provide energy and cost savings.

It is advantageous for platinum in the form of a platinum complex compound to be used as an autocatalyst in an amount of at least 1 wt. %, based on the platinum introduced in the haloplatinum compound.

It is advantageous to add the alkenyl polysiloxane to the solvent or solvent mixture and then to add the haloplatinum compound, since, if they are added in the opposite order, unstable solutions may form, which may continue to react even days after they have been produced.

In the practical application of the process of the invention, divinyltetramethyldisiloxane has been found to be effective as the alkenyl polysiloxane, and hexachloroplatinic (IV) acid has been found to be effective as the haloplatinum compound.

It is also advantageous to wash the filter cake with the solvent or solvent mixture and to combine the second liquid phase obtained in this way with the first liquid phase in order to increase the product yield.

It has been found to be advantageous under practical conditions to use at least one alcohol, especially isopropanol and/or ethanol, as the solvent or solvent mixture.

If the haloplatinum compound is added to the reaction mixture as an anhydrous solution, especially as a solution of the haloplatinum compound in isopropanol, controlled evolution of $CO_2$ gas occurs, which is advantageous, because the gas evolution limits solvent discharge, so that even strict emission limits can be maintained.

It is advisable for the reaction temperature to exceed room temperature, and a reaction temperature above 35° C. is advantageous. The reaction with divinyltetramethyldisiloxane can be carried out especially effectively at a temperature of T=+42° C. to T=+58° C., and a temperature range of T=+48° C. to T=+52° C. has been found to be especially advantageous in practice. In the case of other siloxanes, the temperature can be from T=+42° C. to T=+75° C.

Platinum alkenyl polysiloxane produced by this process, especially platinum divinyltetramethyldisiloxane, is not as darkly colored as the substances produced by the prior-art processes and does not tend to produce unwanted precipitation.

A significant factor that contributes to the positive properties is the use of the actual product as an autocatalyst to produce the product, since this makes it possible to lower the reaction temperature by as much as 20 K or so, which in turn results in the formation of fewer decomposition products and by-products and recovery of the reaction product in less contaminated form.

The invention also concerns the use of the platinum alkenyl polysiloxanes that can be produced by the process, namely, both as hydrosilylation catalysts, a use with which the expert is already familiar, and as autocatalysts in the process of the invention.

EXAMPLES

The invention is illustrated by the following examples:

Example 1

The synthesis is carried out under an inert gas.

42 g of sodium bicarbonate are placed in the apparatus and suspended with 62 mL of divinyltetramethyldisiloxane, 1 g of Pt-siloxane complex, and 150 mL of isopropanol. The suspension is heated to T=+48° C. to +52° C. and then maintained at this temperature while being stirred. A solution of 10 g of Pt as solid $H_2PtCl_6$ in 25 mL of isopropanol is prepared. This solution is then added to the suspension in 5-mL portions. After the addition of each portion, the next portion is not added until the suspension has become colorless again. The temperature is maintained between T=+48° C. and +53° C.

The reaction is exothermic, and strong gas evolution is observed. Stirring of the suspension is continued for at least another 2 h until the suspension becomes colorless. The resulting suspension is cooled to room temperature with continued stirring and then filtered through a G3 fritted glass filter. The filter cake is washed with 75 mL of isopropanol. The solution ("solution 1") is concentrated under vacuum in a rotary evaporator at a maximum temperature of T=+45° C. until no further distillate collection is observed (to a Pt concentration of about 20%). The solution is then filtered through a blue band filter. The filter cake is washed with 200 mL of isopropanol and added to "solution 1" in the next experiment.

Example 2

The synthesis is carried out under an inert gas.

42 g of sodium bicarbonate are placed in the apparatus and suspended with 69 g of trivinylpentamethyltrisiloxane, 2 g of Pt-siloxane complex, and 70 mL of ethanol. A solution of 10 g of Pt as solid $H_2PtCl_6$ in 25 mL of ethanol is prepared. The remainder of the procedure is the same as described in Example 1, except that the reaction temperature is T=+70° C. to T=+75° C., and ethanol is used to wash the filter cake.

Example 3

The synthesis is carried out under an inert gas.

35 g of sodium bicarbonate are placed in the apparatus and suspended with 60 g of divinylhexamethyltrisiloxane, 2 g of Pt-siloxane complex, and 50 mL of ethanol. A solution of 10 g of Pt as solid $H_2PtCl_6$ in 25 mL of ethanol is prepared. The remainder of the procedure is the same as described in Example 1, except that the reaction temperature is T=+70° C. to T=+75° C., and ethanol is used to wash the filter cake.

Example 4

The synthesis is carried out under an inert gas.

37 g of sodium bicarbonate are placed in the apparatus and suspended with 77 g of divinyldiphenyldimethyldisiloxane, 2 g of Pt-siloxane complex, and 50 mL of ethanol. A solution of 10 g of Pt as solid $H_2PtCl_6$ in 25 mL of ethanol is prepared. The remainder of the procedure is the same as described in Example 1, except that the reaction temperature is T=+70° C. to T=+75° C., and ethanol is used to wash the filter cake.

Thus, while there have been shown and described and pointed out fundamental novel features of the present invention as applied to a preferred embodiment thereof, it will be understood that various omissions and substitutions and changes in the form and details of the devices illustrated, and in their operation, may be made by those skilled in the art without departing from the spirit of the present invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature.

It is the intention, therefore, to be limited only as indicated by the scope of the claims appended hereto.

We claim:

1. A process for producing platinum alkenyl polysiloxane complex compounds, comprising the steps of reacting a haloplatinum compound with at least one alkenyl polysiloxane in the initial presence of platinum in the form of a platinum complex compound as an autocatalyst and in the initial presence of at least one base in an organic solvent or mixture of organic solvents that can be oxidized by the haloplatinum compound.

2. A process in accordance with claim 1, including using platinum in the form of a platinum complex compound is used as an autocatalyst in an amount of at least 1 wt. %, based on the platinum introduced in the haloplatinum compound.

3. A process in accordance with claim 1, including first adding the alkenyl polysiloxane to the solvent or solvent mixture, and then adding the haloplatinum compound.

4. A process in accordance with claim 1, wherein the haloplatinum compound is hexachloroplatinic(IV) acid.

5. A process in accordance with claim 1, including using at least one alcohol as the solvent or solvent mixture.

6. A process in accordance with claim 5, wherein at least one of isopropanol and ethanol is used as the alcohol.

7. A process in accordance with claim 1, including adding the haloplatinum compound to the reaction mixture as an anhydrous solution.

8. A process in accordance with claim 7, wherein a solution of the haloplatinum compound in isopropanol is used.

9. A process in accordance with claim 1, including carrying out the reaction at a temperature of T=+42° C. to T=+75° C.

10. A process in accordance with claim 1, including using sodium bicarbonate as the base.

11. A process in accordance with claim 1, further including separating solid particles from a liquid phase and then concentrating the liquid phase to recover the product.

12. A process in accordance with claim 1, wherein the alkenyl polysiloxane is divinyltetramethyldisiloxane.

13. A process in accordance with claim 12, including carrying out the reaction at a temperature of T=+48° C. to T=+52° C.

14. A process for producing platinum alkenyl polysiloxane, comprising the step of using platinum alkenyl polysiloxane as an autocatalyst.

15. A process for producing platinum divinyltetramethyldisiloxane comprising the step of using platinum divinyltetramethyldisiloxane as an autocatalyst.

16. A process in accordance with claim 1, including using platinum alkenyl polysiloxane as the autocatalyst.

17. A process for producing platinum divinyltetramethyldisiloxane, comprising the steps of reacting a haloplatinum compound with platinum divinyltetramethyldisiloxane in the initial presence of platinum in the form of a platinum complex compound as an autocatalyst and in the initial presence of at least one base in an organic solvent or mixture of organic solvents that can be oxidized by the haloplatinum compound.

* * * * *